(12) United States Patent
Druma

(10) Patent No.: US 12,245,806 B2
(45) Date of Patent: Mar. 11, 2025

(54) COOLED BIPOLAR RADIO-FREQUENCY ABLATION PROBE

(71) Applicant: Medtronic Holding Company Sarl, Tolochenaz (CH)

(72) Inventor: Calin Druma, Sunnyvale, CA (US)

(73) Assignee: MEDTRONIC HOLDING COMPANY SARL (CH)

( * ) Notice: Subject to any disclaimer, the term of this patent is extended or adjusted under 35 U.S.C. 154(b) by 870 days.

(21) Appl. No.: 17/410,559

(22) Filed: Aug. 24, 2021

(65) Prior Publication Data

US 2023/0066333 A1   Mar. 2, 2023

(51) Int. Cl.
  A61B 18/14  (2006.01)
  A61B 18/00  (2006.01)
  A61B 18/02  (2006.01)
  A61B 18/12  (2006.01)

(52) U.S. Cl.
  CPC .......... A61B 18/1492 (2013.01); A61B 18/02 (2013.01); A61B 2018/00577 (2013.01); A61B 2018/00821 (2013.01); A61B 2018/0256 (2013.01); A61B 2018/126 (2013.01)

(58) Field of Classification Search
  CPC ........... A61B 2018/00791; A61B 2018/00797; A61B 2018/00815; A61B 2018/00821
  See application file for complete search history.

(56) References Cited

U.S. PATENT DOCUMENTS

| | | | | |
|---|---|---|---|---|
| 5,688,267 A | * | 11/1997 | Panescu ................. | A61N 1/403 606/41 |
| 6,106,524 A | * | 8/2000 | Eggers ................. | A61B 5/0531 606/41 |
| 6,402,742 B1 | * | 6/2002 | Blewett .............. | A61B 18/1477 607/101 |
| 6,506,189 B1 | * | 1/2003 | Rittman, III ....... | A61B 18/1482 606/49 |

(Continued)

FOREIGN PATENT DOCUMENTS

WO   WO2019/231907   12/2019

OTHER PUBLICATIONS

Cooled radiofrequency ablation technology for painful bone tumors, S.A. Angileri et al., Acta Biomed 2020, vol. 91, Supplement 10: e2020007, 2020.

(Continued)

*Primary Examiner* — Ronald Hupczey, Jr.

(57) ABSTRACT

A cooled radio-frequency (RF) ablation probe is provided. The RF ablation probe includes a first tubular portion defining at least part of an internal cavity for circulating coolant through the cooled RF ablation probe; a second tubular portion surrounding the first tubular portion along a first portion of the length of the cooled RF ablation probe; a third tubular portion surrounding the second tubular portion along a second portion of the length of the cooled RF ablation probe; and a fourth tubular portion surrounding the third tubular portion along a third portion of the length of the cooled RF ablation probe. A gap is defined between the third (Continued)

tubular portion and the fourth tubular portion that can be filled with air or a vacuum can be formed in the gap to insulate one or more thermocouples attached to the fourth tubular portion from the coolant in the internal cavity.

20 Claims, 5 Drawing Sheets

(56) References Cited

U.S. PATENT DOCUMENTS

| | | | |
|---|---|---|---|
| 6,858,025 B2 * | 2/2005 | Maurice | A61B 18/02 606/41 |
| 7,077,842 B1 * | 7/2006 | Cosman | A61B 18/148 606/41 |
| 9,956,032 B1 | 5/2018 | Cosman | |
| 2006/0106375 A1 | 5/2006 | Werneth | |
| 2008/0208181 A1 * | 8/2008 | Toubia | A61B 18/02 606/20 |
| 2010/0324546 A1 * | 12/2010 | Levin | A61B 18/02 606/24 |
| 2014/0058378 A1 | 2/2014 | Brannan | |
| 2015/0305799 A1 | 10/2015 | Trieu | |
| 2018/0008345 A1 * | 1/2018 | Williams | A61B 18/1815 |
| 2018/0344383 A1 | 12/2018 | Brannan et al. | |
| 2019/0117298 A1 | 4/2019 | Beeckler | |
| 2019/0343574 A1 | 11/2019 | Lee et al. | |
| 2020/0138502 A1 | 5/2020 | Curley | |
| 2020/0146744 A1 | 5/2020 | Defosset et al. | |
| 2020/0281646 A1 | 9/2020 | Pellegrino et al. | |
| 2021/0045792 A1 | 2/2021 | Wang | |

OTHER PUBLICATIONS

International Search and Written for PCT/EP2022/072300 dated Nov. 30, 2022.

* cited by examiner

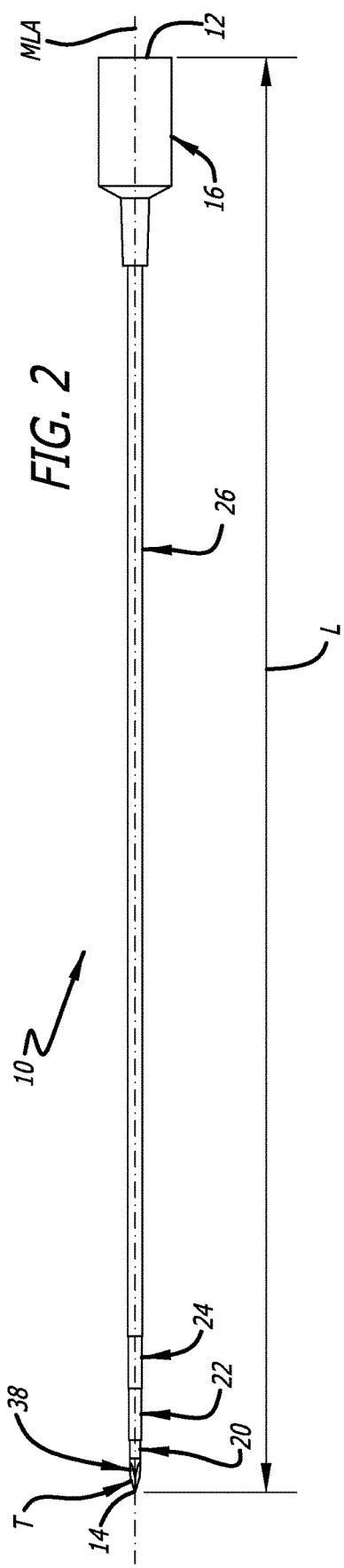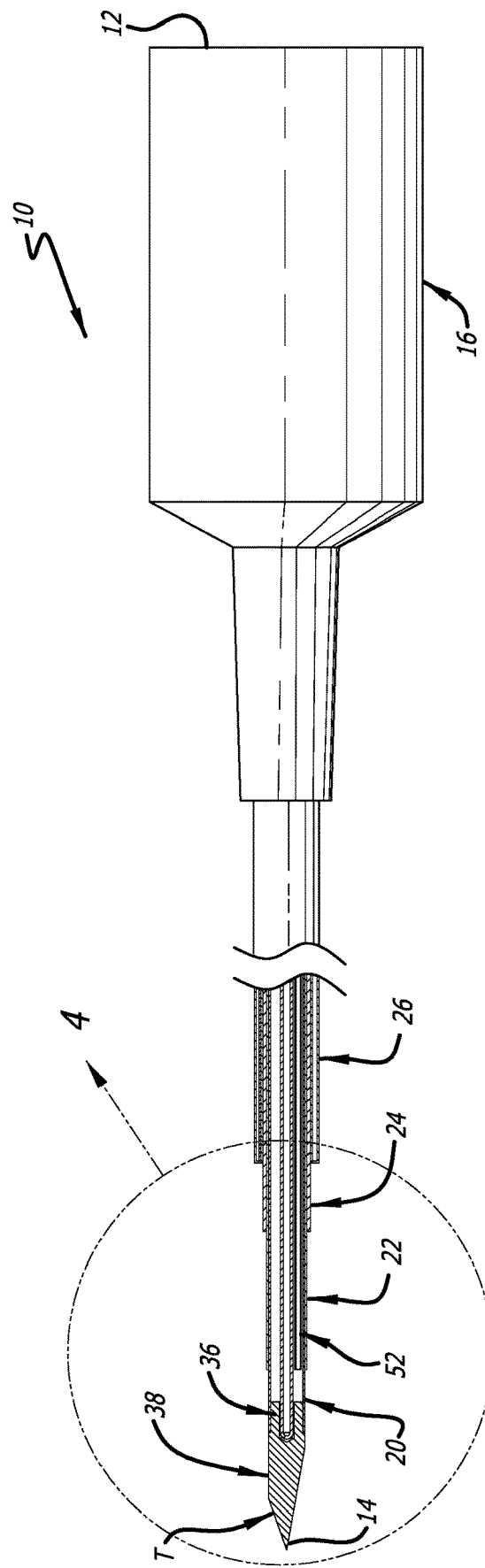

COOLED BIPOLAR RADIO-FREQUENCY ABLATION PROBE

FIELD

The present technology generally relates to a cooled bipolar radio-frequency (RF) ablation probe affording temperature measurements of heating in tissues proximal to return electrode(s), while simultaneously limiting (if not eliminating) adverse effects of cooling effects of water circulated through the cooled RF ablation probe on such temperature measurements.

BACKGROUND

Metastases and corresponding nerve inflammation can cause severe pain in patients having such cancer. Tumor ablation can be used for the palliative treatment of such painful metastases. Currently, RF ablation is used for treating spinal metastases, and there is increased interest in using cooled bipolar RF ablation probes for such ablation. Typical cooled bipolar RF ablation probes use water as a coolant, temperature-sensing devices such as thermocouple(s) are embedded in body portions of the typical cooled bipolar RF ablation probes, and these thermocouple(s) are located distally of return electrode(s). As such, the typical cooled bipolar RF ablation probes typically do not measure heating in tissues proximal to the return electrode(s). Furthermore, such temperature measurements would be difficult to make due to cooling-effects of the water circulated through the typical cooled bipolar RF ablation probes if the thermocouple(s) were adjacent the return electrode(s). Therefore, there is a need for a cooled bipolar RF ablation probe that affords temperature measurements of heating in the tissues proximal to the return electrode(s), while simultaneously limiting (if not eliminating) the adverse effects of the cooling effects of the water circulated therethrough on such temperature measurements.

SUMMARY

The techniques of this disclosure generally relate to a cooled bipolar RF ablation probe.

In one aspect, the present disclosure provides a cooled radio-frequency (RF) ablation probe including a proximal end, an opposite distal end, and a length extending between the proximal end and the distal end; a collar portion positioned at least adjacent the proximal end; a first tubular portion extending from the collar portion toward the distal end, the first tubular portion defining at least part of an internal cavity for circulating coolant through the cooled RF ablation probe; a second tubular portion surrounding the first tubular portion along a first portion of the length of the cooled RF ablation probe; a third tubular portion surrounding the second tubular portion along a second portion of the length of the cooled RF ablation probe; a fourth tubular portion surrounding the third tubular portion along a third portion of the length of the cooled RF ablation probe; a tip portion provided at and adjacent the distal end, the tip portion being spaced apart from the third tubular portion by a portion of the second tubular portion, and a portion of the tip portion being received within the first tubular portion to block off the internal cavity defined at least in part by the first tubular portion; and at least one temperature sensor provided within or on a portion of the fourth tubular portion; where at least a portion of the tip portion serves as an active electrode, and at least a portion of the third tubular portion serves as a return electrode; and where a gap is defined between the third tubular portion and the fourth tubular portion that extends between a first position and a second position along the length of the RF ablation probe, the first position being closer to the proximal end than the second position, the gap being blocked off at or adjacent the first position and at or adjacent the second position so that the gap can be filled with air or a vacuum can be formed in the gap.

In another aspect, the present disclosure provides a cooled radio-frequency (RF) ablation probe including a proximal end, an opposite distal end, and a length extending between the proximal end and the distal end; a first tubular portion extending between the proximal end and the distal end, the first tubular portion defining at least part of an internal cavity for circulating coolant through the cooled RF ablation probe; a second tubular portion surrounding the first tubular portion along a first portion of the length of the cooled RF ablation probe; a third tubular portion surrounding the second tubular portion along a second portion of the length of the cooled RF ablation probe; a fourth tubular portion surrounding the third tubular portion along a third portion of the length of the cooled RF ablation probe; a tip portion provided at and adjacent the distal end, a portion of the tip portion defining at least part of the internal cavity; and at least one temperature sensor provided within or on a portion of the fourth tubular portion; where at least a portion of the tip portion serves as an active electrode, and at least a portion of the third tubular portion serves as a return electrode; and wherein a gap is defined between the third tubular portion and the fourth tubular portion that extends between a first position and a second position along the length of the RF ablation probe, the first position being closer to the proximal end than the second position, the gap being blocked off at or adjacent the first position and at or adjacent the second position so that the gap can be filled with air or a vacuum can be formed in the gap.

In yet another aspect, the present disclosure provides a cooled radio-frequency (RF) ablation probe including a proximal end, an opposite distal end, and a length extending between the proximal end and the distal end; a collar portion positioned at least adjacent the proximal end; a first tubular portion extending from the collar portion toward the distal end, the first tubular portion defining at least part of an internal cavity for circulating coolant through the cooled RF ablation probe; a second tubular portion surrounding the first tubular portion along a first portion of the length of the cooled RF ablation probe; a third tubular portion surrounding the second tubular portion along a second portion of the length of the cooled RF ablation probe; a fourth tubular portion surrounding the third tubular portion along a third portion of the length of the cooled RF ablation probe; a coolant supply line extending from the collar portion through at a first portion of the internal cavity toward the distal end, the coolant supply line configured to expel the coolant into the internal cavity; a tip portion provided at and adjacent the distal end, the tip portion being spaced apart from the third tubular portion by a portion of the second tubular portion, and a portion of the tip portion being received within the first tubular portion to block off the internal cavity defined at least in part by the first tubular portion; and at least one monitoring thermocouple provided within or on a portion of the fourth tubular portion; where at least a portion of the tip portion serves as an active electrode, and at least a portion of the third tubular portion serves as a return electrode; and where a gap is defined between the third tubular portion and the fourth tubular portion that extends between a first position and a second position along the length of the RF ablation probe, the first position being closer to the proximal end than the second position, the gap being blocked off at or adjacent the first position and at or adjacent the second position so that the gap can be filled with air or a vacuum can be formed in the gap.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 2 is a side elevational view that illustrates the bipolar RF ablation probe of FIG. 1;

FIG. 3 is an enlarged side, fragmentary, partially cross-sectional view of the bipolar RF ablation probe of FIG. 1;

DETAILED DESCRIPTION

A cooled bipolar RF ablation probe in accordance with a preferred embodiment of the present disclosure is generally indicated by the numeral 10 in FIGS. 1-6. The RF ablation probe 10 includes a proximal end 12, an opposite distal end 14, a length L between the proximal end 12 and the distal end 14, and a mid-longitudinal axis MLA extending along the length and through the proximal end 12 and the distal end 14. As discussed below, the RF ablation probe 10 is a bipolar ablation probe, and includes at least two electrodes (an active (or energized) electrode and a return electrode) facilitating application of RF energy such as, for example, electrical current to hard and/or soft tissues adjacent the RF ablation probe.

Figure 1:
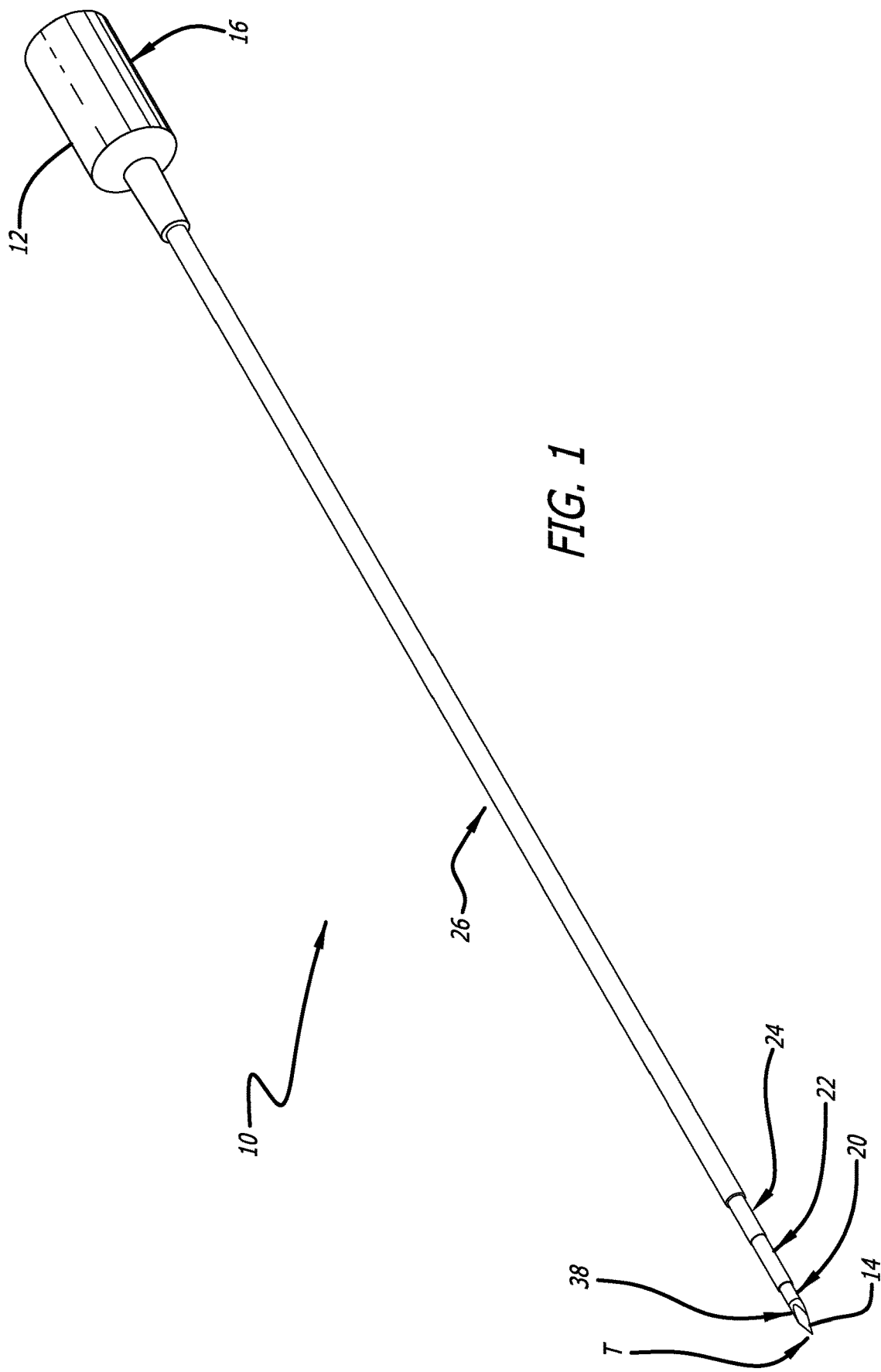
FIG. 1 is a top, side perspective view that illustrates a bipolar RF ablation probe according to an embodiment of the present disclosure.

As depicted in FIGS. 1-3, the RF ablation probe 10 includes collar portion 16, a first tubular portion 20, a second tubular portion 22, a third tubular portion 24, a fourth tubular portion 26, and a tip portion T. The collar portion 16 is provided at and adjacent the proximal end 12. Furthermore, portions of the first tubular portion 20, the second tubular portion 22, the third tubular portion 24, and/or the fourth tubular portion 26 can extend within and through the collar portion 16, and, as depicted in FIGS. 1-3, can extend outwardly relative to the collar portion 16 toward the distal end 14. And the tip portion T is provided at and adjacent the distal end 14.

As discussed below, portions of the tip portion T serve as a portion of the active electrode, portions of the first tubular portion 20 serve as another portion of the active electrode and afford circulation of coolant through the RF ablation probe 10, portions of the second tubular portion 22 serve as an insulator insulating the active electrode and the return electrode from one another, portions of the third tubular portion 24 serve as the return electrode and define a portion of an insulative gap $G_1$, and portions of the fourth tubular portion 26 serve as a sleeve adjacent the third tubular portion and define another portion of the insulative gap $G_1$.

Portions of the first tubular portion 20, the second tubular portion 22, the third tubular portion 24, and/or the fourth tubular portion 26 can each be cylindrical and/or extend coaxially with one another. As depicted in FIGS. 3-6, portions of the first tubular portion 20 can extend within and through portions of the second tubular portion 22, portions of the second tubular portion 22 can extend within and through portions of the third tubular portion 24, and portions of the third tubular portion 24 can extend within and through portions of the fourth tubular portion 26. In other words, portions of the second tubular portion 22 can encompass portions of the first tubular portion 20, portions of the third tubular portion 24 can encompass portions of the second tubular portion 22, and portions of the fourth tubular portion 26 can encompass portions of the third tubular portion 24. As such, the first tubular portion 20 is the innermost of these tubular portions, the second tubular portion 22 is intermediate the first tubular portion 20 and the third tubular portion 24, and the third tubular portion 24 is intermediate the second tubular portion 22 and the fourth tubular portion 24, and fourth tubular portion 24 is the outermost of these tubular portions.

The insulative gap $G_1$ can be formed between the third tubular portion 24 and the fourth tubular portion 26. The insulative gap $G_1$ can extend between the third tubular portion 24 and the fourth tubular portion 26 along all or portions of a span in which the third tubular portion 24 extends through the fourth tubular portion 26. Furthermore, if the third tubular portion 24 and the fourth tubular portion 26 are cylindrical and coaxial along all or portions thereof, the insulative gap $G_1$ can also be cylindrical and extend around an exterior surface $S_1$ of the third tubular portion 24 and an interior surface $S_2$ of the fourth tubular portion 26 along all or portions of the span in which the third tubular portion 24 extends through the fourth tubular portion 26.

Figure 6:
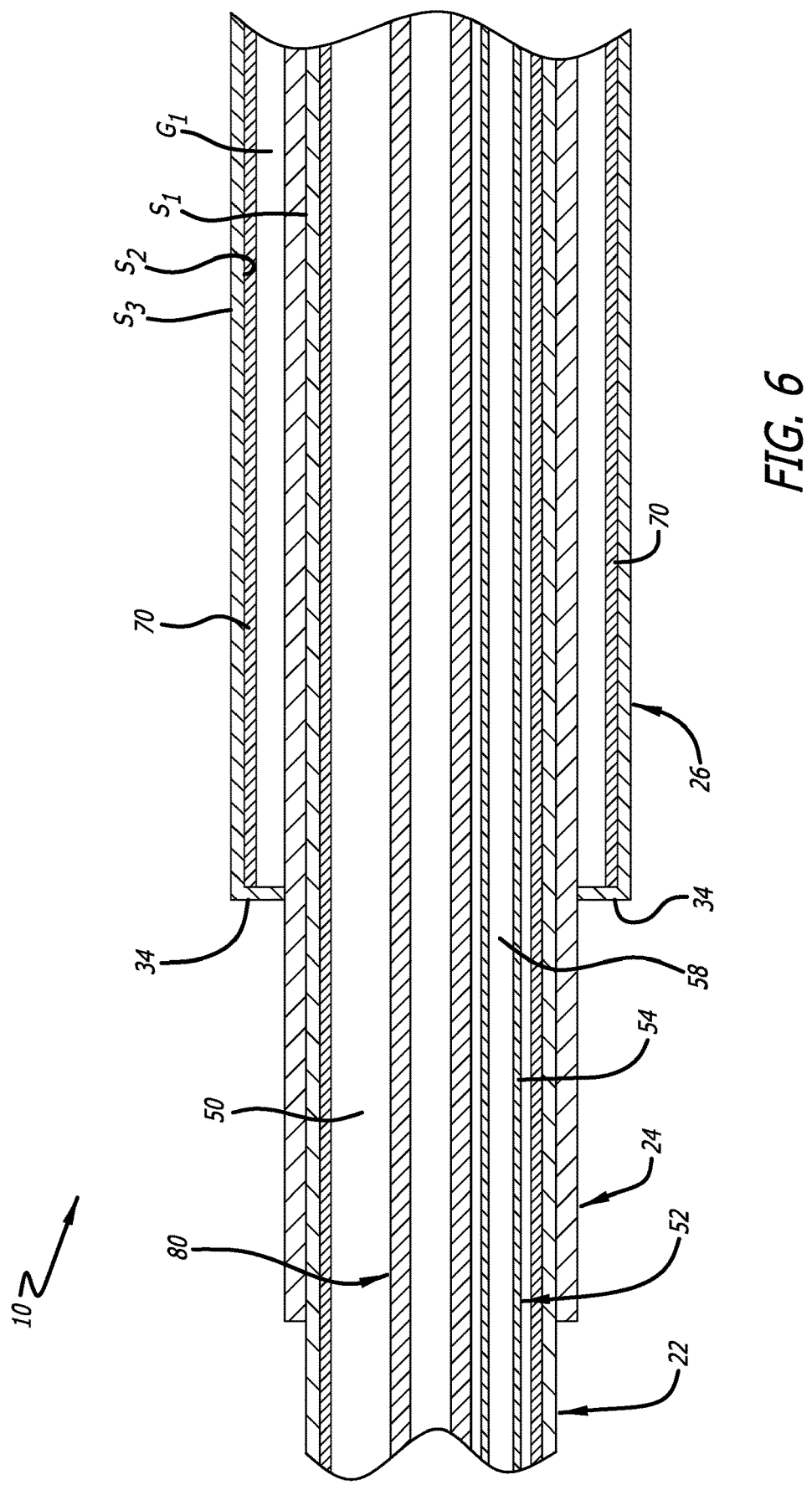
FIG. 6 is an enlarged side, cross-sectional view of the bipolar RF ablation probe of FIG. 1 of the area denoted in FIG. 4.

The insulative gap $G_1$ can be sealed and/or blocked off at a proximal end thereof by portions of the collar portion 16, and, as depicted in FIG. 6, can be sealed and/or blocked off at a distal end thereof by a portion 34 of the fourth tubular portion 26 extending in a direction transverse to the mid-longitudinal axis MLA that is attached relative to the third tubular portion 24. Another portion of the fourth tubular portion 26 extending in a direction transverse to the mid-longitudinal axis MLA similar to the portion 34 can be used to seal or block off the proximal end of the insulative gap $G_1$. The portion 34 and/or the another portion of the fourth tubular portion 26 similar to the portion 34 can, for example, be attached and sealed to the exterior surface $S_1$ using adhesives, brazing, soldering, welding, and/or crimping thereof to the exterior surface $S_1$.

Air can be provided or a vacuum can be formed in the insulative gap $G_1$ to create an insulative layer between the third tubular portion 24 and the fourth tubular portion 26. As discussed below, one or more thermocouples can be positioned on the fourth tubular portion 26. The insulation afforded by the insulative gap $G_1$ can be used in insulating the thermocouple(s) positioned on the fourth tubular portion 26 from other portions of the RF ablation probe 10 and the cooling effects of the coolant circulated through the RF ablation probe 10, and these thermocouple(s) can be used in determining the temperature of hard and/or soft tissues adjacent thereto.

Figure 4:
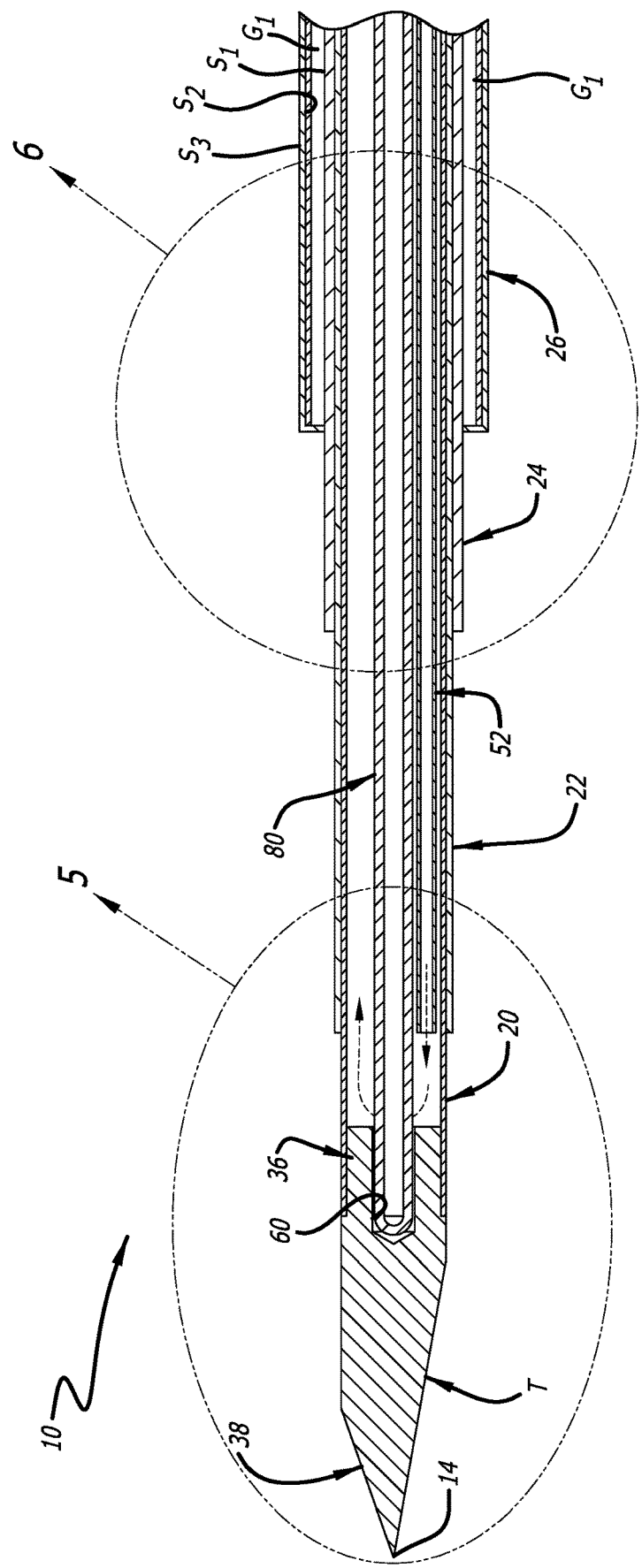
FIG. 4 is an enlarged side, cross-sectional view of the bipolar RF ablation probe of FIG. 1.

While gap $G_1$ is depicted in FIGS. 4 and 6 as extending completely around the RF ablation probe 10 between the third tubular portion 24 and the fourth tubular portion 26, the gap $G_1$ is not limited thereto. The gap $G_1$ can be interrupted around the RF ablation probe 10 to one or more individual gaps around the third tubular portion 24 that can afford the above-described insulation for thermocouple(s) provided in these various individual gaps. To illustrate, the individual gap(s) can be formed at different radial positions around the third tubular portion 24, and these individual gaps can be formed by section(s) of the fourth tubular portion 26 and sidewalls along the longitudinal and radial edges of these section(s) attached to the third tubular portion 24.

Furthermore, additional gaps can be formed adjacent the gap $G_1$ by adding additional sleeve layers adjacent the fourth tubular portion 26. For example, a second gap could be formed by adding a fifth tubular portion attached to and proximate the fourth tubular portion 26 and leaving space therebetween for the second gap, and a third gap could be formed by adding a sixth tubular portion attached to and proximate the fifth tubular portion and leaving a space therebetween for the third gap. The fifth tubular portion and the sixth tubular portion could have similar configuration and attached in similar fashion to the fourth tubular portion 26, and the second and third gaps likewise could be formed in similar fashion to the gap $G_1$.

Additionally, all or portions of the exterior surface $S_1$ of the third tubular portion 24 adjacent the fourth tubular portion 24 can have smaller dimensions than other portions of the third tubular portion 24. To illustrate, when the third tubular portion 24 is cylindrical, all or portions of the exterior surface $S_1$ adjacent the fourth tubular portion 26 could have smaller diameters than the other portions of the third tubular portion 24. As such, all or portions of the exterior surface $S_1$ adjacent the fourth tubular portion 26 could be indented relative to the other portions of the exterior surface $S_1$. When the insulative gap $G_1$ is formed as described above, the overall size of the insulative gap $G_1$ can be increased by these smaller dimensions of the exterior surface $S_1$ of the third tubular portion 24 adjacent the fourth tubular portion 26.

Figure 5:
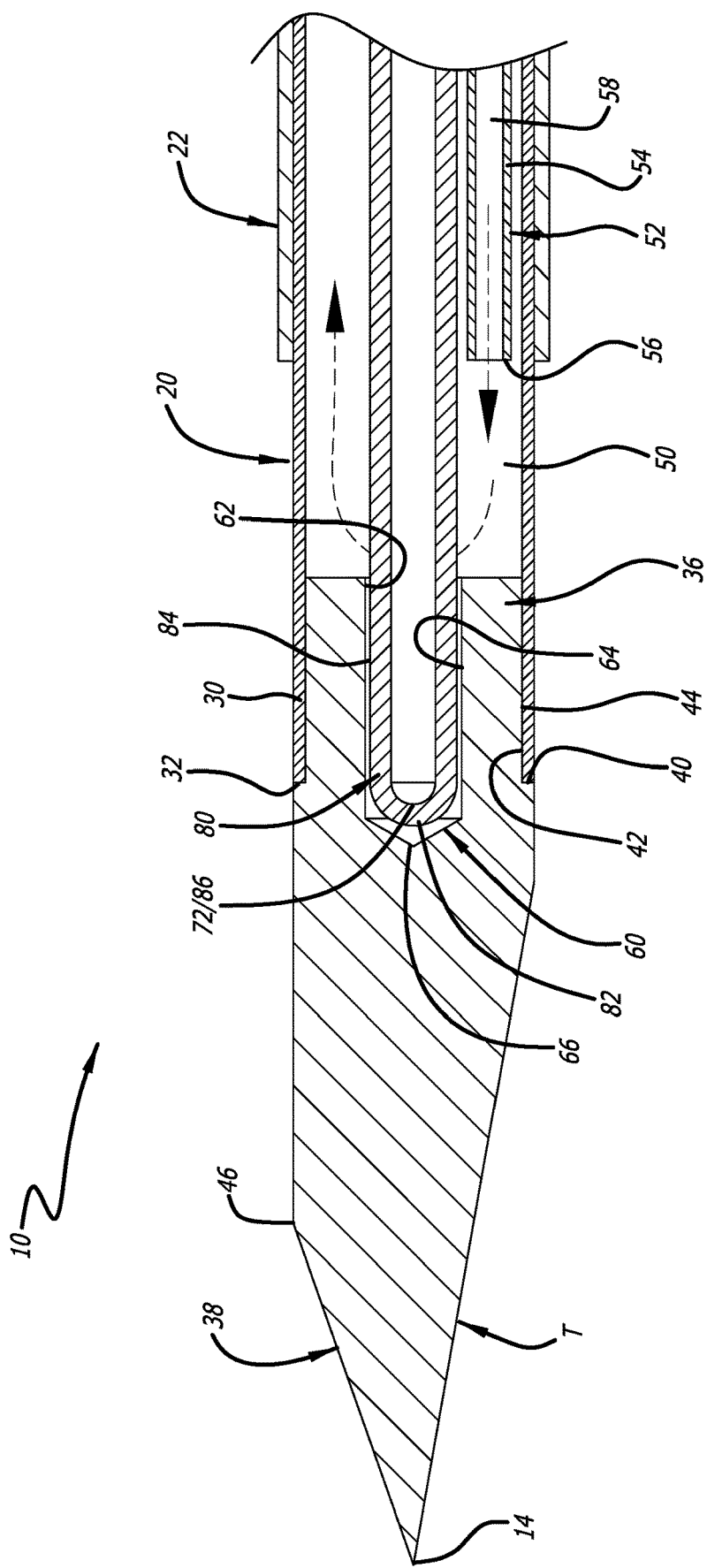
FIG. 5 is an enlarged side, cross-sectional view of the bipolar RF ablation probe of FIG. 1 of the area denoted in FIG. 4.

The first tubular portion 20 extends from the collar portion 16, and, as depicted in FIG. 5, terminates at a distal end portion 30 having a distal end 32. Portions of the tip portion T can be attached to the distal end portion 30 of the first tubular portion 20, and portions of the tip portion T can have various shapes that can be configured to penetrate hard and/or soft tissues of in a body. As depicted in FIGS. 4 and 5, the tip portion T can include a first portion 36, a second portion 38, and a shoulder portion 40 positioned between the first portion 36 and the second portion 38. The tip portion T can be attached to the first tubular portion 20 via receipt of the first portion 36 in the first tubular portion 20. As discussed below, portions of the tip portion T (and portions of the first tubular portion 20 adjacent the tip portion T) can serve the active electrode to facilitate application of the RF energy (such as, for example, electrical current) to hard and/or soft tissues adjacent the RF ablation probe. Furthermore, the penetration of hard and/or soft tissues can be afforded by the configuration of the second portion 38.

As depicted in FIG. 5, the first portion 36 can be inserted into the distal end portion 30 of the first tubular portion 20 until the distal end 32 contacts the shoulder portion 40. A fluid-tight connection can be formed between the first tubular portion 20 and the tip portion T via, for example, an interference fit of an interior surface 42 of the distal end portion 30 with an exterior surface 44 of the first portion 36. Additionally, adhesives, brazing, soldering, and/or welding between the interior surface 42 and the exterior surface 44 can be used instead of or in addition to the interference fit to form the fluid-tight connection between the first tubular portion 20 and the tip portion T.

As depicted in FIGS. 4 and 5, the second portion 38 can include an exterior surface 46 shaped to facilitate penetration of hard and/or soft tissues. That is, the exterior surface 46 can be configured to cut through hard and/or soft tissues to afford penetration of the RF ablation probe 10 therethrough. These shapes for facilitating penetration can, for example, include those that are identical or similar to pencil-tip shapes and trocar shapes. As depicted in FIGS. 4 and 5, the exterior surface 46 of the second portion 38 has a generally trocar-like shape to facilitate such penetration.

Portions of the first tubular portion 20 along with portions of the collar portion 16 and the tip portion T can define portions of an interior cavity 50 of the RF ablation probe 10. The interior cavity 50 can be used for circulating the coolant to facilitate cooling of portions of the RF ablation probe 10. The coolant can, for example, be water, and the coolant circulated through the interior cavity 50 is used to remove heat from the RF ablation probe 10 generated via operation the active electrode (formed by portions of the first tubular portion 20 and the tip portion T) and the return electrode (formed by the third tubular portion 24).

A supply line 52 can extend through portions of the interior cavity 50 to supply the coolant thereto. For example, the supply line 52 can extend from the collar portion 16 through portions of the interior cavity 50. As depicted in FIGS. 4 and 5, the supply line 52 extends to at least adjacent the tip portion T. The supply line 52 includes a tubular portion 54 including a distal end 56. The supply line 52 also includes an interior cavity 58 affording flow of the coolant therethrough, and the coolant can be expelled from the interior cavity 58 at the distal end 56 of the supply line 52.

In addition to the supply line 52, a return port (not shown) and/or a return line (not shown) can be provided in or fluidly communicate with the interior cavity 50 to remove the coolant supplied thereto. To illustrate, the return port can provided in the collar portion 16 and the return line can extend from the collar portion 16 through portions of the interior cavity 50. Suction can be applied to the return port/line to facilitate removal of the coolant from the interior cavity 50.

Portions of the supply line 52 and/or the return port/line can extend to, into, and/or through the collar portion 20, and connections (not shown) can be provided inside or outside of the collar portion 20 that interconnect and provide fluid communication of the supply line 52 and the return port/line with an upstream coolant supply line (not shown) and a downstream coolant water return line (not shown), respectively.

Adjacent the interior cavity 50, the tip portion T, as depicted in FIG. 5, includes an interior depression 60 that is oriented toward the proximal end 12. The interior depression 60 includes a proximal opening 62, a sidewall or sidewalls 64, and a distal wall 66. As discussed below, one or more thermocouples can be positioned in the interior depression 60 and contact portions of the tip portion T via contact with the sidewall(s) and/or distal wall 66. The contact of these thermocouple(s) positioned in the interior depression 60 with the tip portion T can be used in determining the temperature of the tip portion T.

The RF ablation probe 10 can include one or more temperature sensors in the form of one or more monitoring thermocouples 70 (positioned on the fourth tubular portion 26) and one or more control thermocouples 72 (positioned in the interior depression 60). The monitoring thermocouple(s) 70 and the control thermocouple(s) 72 can be used to determine temperature(s) at various locations with respect to the RF ablation probe 10. The temperature(s) sensed by the monitoring thermocouple(s) 70 and the control thermocouple(s) 72 can be used to control operation of the RF ablation probe 10. For example, the monitoring thermocouple(s) 70 can be used to sense temperatures of hard and/or soft tissues adjacent thereto, and the control thermocouple(s) 72 can be used to sense temperatures at the tip portion T. If the temperatures sensed by the monitoring thermocouple(s) 70 and/or the control thermocouple(s) 72 exceed certain thresholds, ablation of these hard and/or soft tissues can be discontinued.

The monitoring thermocouple(s) 70, as depicted in FIG. 6, can be provided on the interior surface $S_2$ adjacent the gap $G_1$. And some of these monitoring thermocouple(s) 70 can be located proximal the portion of the third tubular portion 24 serving as the return electrode. For example, multiple monitoring thermocouples 70 can be arranged in an array on the interior surface $S_2$ of the fourth tubular portion 26 with each of the monitoring thermocouples 70 being equally spaced from one another. As discussed above, the fourth tubular portion 26 is insulated from the coolant by the insulative gap $G_1$, and thus, the insulative gap $G_1$ can also be used to insulate the monitoring thermocouple(s) 70 provided on the interior surface $S_2$ from the coolant circulated through the RF ablation probe 10. Such insulation affords the monitoring thermocouple(s) 70 provided on the interior surface $S_2$ to act as monitoring temperature sensor(s) by more accurately measuring temperature readings of hard and/or soft tissues adjacent the fourth tubular portion 26 and these thermocouple(s) 70. One or more wires connecting the thermocouple(s) 70 to controls of the RF ablation probe 10 can extend through the gap $G_1$ to facilitate relay of the corresponding temperature signals thereto. One or more of the monitoring thermocouples can instead of or in addition to those provided on the interior surface $S_2$ be provided on an exterior surface $S_3$ of the fourth tubular portion 26, and these thermocouple(s) would likewise be insulated from the coolant circulated through the RF ablation probe 10.

The control thermocouple(s) 72, as depicted in FIG. 5, can be provided in interior portions of the RF ablation probe 10 including in the interior depression 60 of the tip portion T. A thermocouple tube 80 extends through the interior cavity 50 from the collar portion 16 to the tip portion T. As depicted in FIG. 5, the thermocouple tube 80 can be connected to the tip portion T via receipt of a distal end portion 82 in the interior depression 60. A connection can be formed between the thermocouple tube 80 and the tip portion T via, for example, an interference fit of an exterior surface 84 of the distal end portion 82 with the sidewall(s) 64 of the interior depression 60. Furthermore, adhesives, brazing, soldering, and/or welding between the exterior surface 84 of the distal end portion 82, and the sidewall(s) 64 and/or the distal wall 66 can be used instead of or in addition to the interference fit to form the connection between thermocouple tube 80 and the tip portion T.

The thermocouple tube 80 itself and/or another thermocouple 86 can be used as the control thermocouple(s) 72. The thermocouple 86 can provided in the interior depression 60 between portions of the exterior surface 84 of the distal end portion 82, and the sidewall(s) 64 and/or the distal wall 66. And the thermocouple 86 can be attached to the sidewall(s) 64 and/or the distal wall 66 via adhesives, brazing, soldering, and/or welding. As such, the distal end portion 82 of the thermocouple tube 80 and/or the thermocouple 86 provided in the interior depression 60 can be in contact with the tip portion T to facilitate temperature measurement thereof. One or more wires connecting the thermocouple tube 80 and/or the thermocouple 86 to the controls of the RF ablation probe 10 can extend through the thermocouple tube 80 to facilitate relay of the corresponding temperature signals thereto Portions of the tip portion T and the first tubular portion 20 adjacent the tip portion T, as discussed above, can serve as the active electrode for applying RF energy (such as, for example, electrical current) to ablate hard and/or soft tissues adjacent thereto. Furthermore, portions of the third tubular portion 24 can serve as the return electrode to facilitate operation of portions of the tip portion T and the first tubular portion 20 adjacent the tip portion T as the active electrode. All or portions of the tip portion T and the first tubular portion 20 can be made of conductive materials such as, for example, metals and metallic alloys including stainless steel and/or Nitinol to facilitate operation as the active electrode. Electrical current can be supplied to the tip portion T via conductivity of the first tubular portion 20. Furthermore, all or portions of the third tubular portion 24 also be made of conductive materials such as, for example, metals and metallic alloys including stainless steel and/or Nitinol to facilitate operation as the return electrode. The second tubular portion 22 can be made of a dielectric materials such as, for example, polyimide, Nylon, and/or PET to insulate the first tubular portion 20 and the third tubular portion 24 from one another.

During use of the RF ablation probe 10, heat is generated by the application of RF energy (such as, for example, electrical current) to hard and/or soft tissues adjacent portions of tip portion T and the first tubular portion 20 adjacent the tip portion T. Excessive heat can be an unwanted byproduct of such ablation, and the coolant circulating through the interior cavity 50 can be used to remove such heat. Before, during, and/or after energization of the tip portion T, the coolant can enter the supply line 52 from the upstream coolant supply line, the coolant can travel through the interior cavity 58 of the supply line 52, the coolant can exit the interior cavity 58 at the distal end 56 of the supply line 52 into the interior cavity 50, and the coolant can circulate through the interior cavity 50 before being removed therefrom. Before, during, and/or after application of the RF energy to the hard and/or soft tissues using portions of the tip portion T and the first tubular portion 20 adjacent the tip portion T, the coolant circulating through the interior cavity serves to remove excessive heat and cool portions of the RF ablation probe 10. The heated coolant can then be removed through the return port/line and the downstream coolant return line. This process can be repeated during use of the RF ablation probe 10 to cool the RF ablation probe 10 during operation thereof.

During use, the temperatures adjacent to the monitoring thermocouple(s) 70 and/or the control thermocouple(s) 72 can be measured thereby in order to ascertain if these temperatures exceed certain thresholds. If the temperatures measured by the monitoring thermocouple(s) 70 and/or the control thermocouple(s) 72 exceed such thresholds, ablation of these hard and/or soft tissues can be modulated by terminating or interrupting operation of the RF ablation probe 10. Furthermore, the circulation of the coolant can also be modulated, if necessary, via termination or interruption to afford more accurate temperature readings by the monitoring thermocouple(s) 70 and/or the control thermocouple(s) 72.

Use of the insulative gap $G_1$ serves in insulating (by in effect shielding) portions of the fourth tubular portion 26 and the monitoring thermocouple(s) 70 provided thereon from the cooling effects of the coolant circulated through the interior cavity 50. The insulative gap $G_1$ creates thermal resistance between the coolant circulating through the interior cavity 50, and the fourth tubular portion 26, the monitoring thermocouple(s) 70, and hard and/or soft tissues adjacent the monitoring thermocouple(s) 70. As such, use of the insulative gap $G_1$ affords more direct temperature measurement by the monitoring thermocouple(s) 70 of hard and/or soft tissues adjacent the monitoring thermocouple(s) 70 with limited (if any) effects of the coolant being circular through the RF ablation probe 10. Such temperature measurements can occur when the electrode formed by the tip portion T is activated or deactivated and/or the circulation of the coolant through the interior cavity is activated or deactivated.

It should be understood that various aspects disclosed herein may be combined in different combinations than the combinations specifically presented in the description and the accompanying drawings. It should also be understood that, depending on the example, certain acts or events of any of the processes of methods described herein may be performed in a different sequence, may be added, merged, or left out altogether (e.g., all described acts or events may not be necessary to carry out the techniques). In addition, while certain aspect of this disclosure are described as being performed by a single module or unit for purposes of clarity, it should be understood that the techniques of this disclosure may be performed by a combination of units or modules associated with, for example, a medical device.

I claim:

1. A cooled radio-frequency (RF) ablation probe comprising:
    a proximal end, an opposite distal end, and a length extending between the proximal end and the distal end;
    a collar portion positioned at least adjacent the proximal end;
    a first tubular portion extending from the collar portion toward the distal end, the first tubular portion defining at least part of an internal cavity for circulating coolant through the cooled RF ablation probe;
    a second tubular portion surrounding the first tubular portion along a first portion of the length of the cooled RF ablation probe;
    a third tubular portion surrounding the second tubular portion along a second portion of the length of the cooled RF ablation probe;
    a fourth tubular portion surrounding the third tubular portion along a third portion of the length of the cooled RF ablation probe;
    a tip portion provided at and adjacent the distal end, the tip portion being spaced apart from the third tubular portion by a portion of the second tubular portion, and a portion of the tip portion being received within the first tubular portion to block off the internal cavity defined at least in part by the first tubular portion; and
    at least one temperature sensor provided within or on a portion of the fourth tubular portion;
    wherein at least a portion of the tip portion serves as an active electrode, and at least a portion of the third tubular portion serves as a return electrode; and
    wherein a gap is defined between the third tubular portion and the fourth tubular portion that extends between a first position and a second position along the length of the RF ablation probe, the first position being closer to the proximal end than the second position, the gap being blocked off at or adjacent the first position and at or adjacent the second position so that the gap can be filled with air or a vacuum can be formed in the gap.

2. The cooled RF ablation probe of claim 1, wherein the at least one temperature sensor is at least one monitoring thermocouple.

3. The cooled RF ablation probe of claim 1, wherein the air-filled or vacuumed gap serves to insulate the at least one temperature sensor from the coolant circulated through the internal cavity of the first tubular portion.

4. The cooled RF ablation probe of claim 1, wherein the gap between the third tubular portion and the fourth tubular portion extends completely around the RF ablation probe.

5. The cooled RF ablation probe of claim 1, wherein a coolant supply line extends from the collar portion through at least a first portion of the internal cavity toward the distal end, the coolant supply line configured to dispense the coolant into the internal cavity for circulation therethrough.

6. The cooled RF ablation probe of claim 5, wherein the coolant is removed from the internal cavity by a coolant return line or port extending through the collar portion.

7. The cooled RF ablation probe of claim 1, further comprising a thermocouple tube extending from the collar portion to the tip portion, wherein the thermocouple tube includes a distal end portion having a distal end, and the tip portion includes a depression oriented toward the internal cavity, at least a portion of the distal end portion being received in the depression.

8. The cooled RF ablation prove of claim 7, wherein a control thermocouple is provided in the depression adjacent the distal end of the distal end portion of the thermocouple tube.

9. A cooled radio-frequency (RF) ablation probe comprising:
    a proximal end, an opposite distal end, and a length extending between the proximal end and the distal end;
    a first tubular portion extending between the proximal end and the distal end, the first tubular portion defining at least part of an internal cavity for circulating coolant through the cooled RF ablation probe;
    a second tubular portion surrounding the first tubular portion along a first portion of the length of the cooled RF ablation probe;
    a third tubular portion surrounding the second tubular portion along a second portion of the length of the cooled RF ablation probe;
    a fourth tubular portion surrounding the third tubular portion along a third portion of the length of the cooled RF ablation probe;
    a tip portion provided at and adjacent the distal end, a portion of the tip portion defining at least part of the internal cavity; and
    at least one temperature sensor provided within or on a portion of the fourth tubular portion;
    wherein at least a portion of the tip portion serves as an active electrode, and at least a portion of the third tubular portion serves as a return electrode; and
    wherein a gap is defined between the third tubular portion and the fourth tubular portion that extends between a first position and a second position along the length of the RF ablation probe, the first position being closer to the proximal end than the second position, the gap being blocked off at or adjacent the first position and at or adjacent the second position so that the gap can be filled with air or a vacuum can be formed in the gap.

10. The cooled RF ablation probe of claim 9, wherein the at least one temperature sensor is at least one monitoring thermocouple.

11. The cooled RF ablation probe of claim 9, wherein the air-filled or vacuumed gap serves to insulate the at least one temperature sensor from the coolant circulated through the internal cavity of the first tubular portion.

12. The cooled RF ablation probe of claim 9, wherein the gap between the third tubular portion and the fourth tubular portion extends completely around the RF ablation probe.

13. The cooled RF ablation probe of claim 9, wherein a coolant supply line extends from the at least adjacent the proximal end through at least a first portion of the internal cavity toward the distal end, the coolant supply line configured to dispense the coolant into the internal cavity for circulation therethrough.

14. The cooled RF ablation probe of claim 13, wherein the coolant is removed from the internal cavity by a coolant return line or port provided at the proximal end of the RF ablation probe.

15. The cooled RF ablation probe of claim 9, further comprising a thermocouple tube extending from the proximal end to the tip portion, wherein the thermocouple tube includes a distal end portion having a distal end, and the tip portion includes a depression oriented toward the internal cavity, at least a portion of the distal end portion being received in the depression.

16. The cooled RF ablation prove of claim 15, wherein a control thermocouple is provided in the depression adjacent the distal end of the distal end portion of the thermocouple tube.

17. A cooled radio-frequency (RF) ablation probe comprising:
   a proximal end, an opposite distal end, and a length extending between the proximal end and the distal end;
   a collar portion positioned at least adjacent the proximal end;
   a first tubular portion extending from the collar portion toward the distal end, the first tubular portion defining at least part of an internal cavity for circulating coolant through the cooled RF ablation probe;
   a second tubular portion surrounding the first tubular portion along a first portion of the length of the cooled RF ablation probe;
   a third tubular portion surrounding the second tubular portion along a second portion of the length of the cooled RF ablation probe;
   a fourth tubular portion surrounding the third tubular portion along a third portion of the length of the cooled RF ablation probe;
   a coolant supply line extending from the collar portion through at a first portion of the internal cavity toward the distal end, the coolant supply line configured to expel the coolant into the internal cavity;
   a tip portion provided at and adjacent the distal end, the tip portion being spaced apart from the third tubular portion by a portion of the second tubular portion, and a portion of the tip portion being received within the first tubular portion to block off the internal cavity defined at least in part by the first tubular portion; and
   at least one monitoring thermocouple provided within or on a portion of the fourth tubular portion;
   wherein at least a portion of the tip portion serves as an active electrode, and at least a portion of the third tubular portion serves as a return electrode; and
   wherein a gap is defined between the third tubular portion and the fourth tubular portion that extends between a first position and a second position along the length of the RF ablation probe, the first position being closer to the proximal end than the second position, the gap being blocked off at or adjacent the first position and at or adjacent the second position so that the gap can be filled with air or a vacuum can be formed in the gap.

18. The cooled RF ablation probe of claim 17, wherein the air-filled or vacuumed gap serves to insulate the at least one temperature sensor from the coolant circulated through the internal cavity of the first tubular portion.

19. The cooled RF ablation probe of claim 17, wherein the gap between the third tubular portion and the fourth tubular portion extends completely around the RF ablation probe.

20. The cooled RF ablation prove of claim 17, wherein a control thermocouple is provided in a depression formed in the tip portion, the depression being oriented toward the internal cavity.

* * * * *